United States Patent [19]

Benker et al.

[11] 4,275,200

[45] Jun. 23, 1981

[54] PROCESS FOR THE PRODUCTION OF OXAZOLINONE-2-COMPOUNDS

[75] Inventors: Fritz Benker, Pullach; Hans-Heinrich Credner, Hohenschaeftlarn; Wolfgang Lässig, Munich; Ernst Meier, Munich; Siegfried Schleger, Munich, all of Fed. Rep. of Germany

[73] Assignee: AGFA-Gevaert, A.G., Leverkusen, Fed. Rep. of Germany

[21] Appl. No.: 910,624

[22] Filed: May 30, 1978

Related U.S. Application Data

[63] Continuation of Ser. No. 725,323, Sep. 22, 1976, abandoned.

[30] Foreign Application Priority Data

Sep. 26, 1975 [DE] Fed. Rep. of Germany ....... 2543094

[51] Int. Cl.³ ................. C07D 263/20; C07D 295/00; C07D 213/02

[52] U.S. Cl. ................... 544/137; 546/275; 548/200; 548/229; 548/232

[58] Field of Search .................. 260/307 C; 548/229, 548/232, 200; 544/137; 546/275

[56] References Cited

PUBLICATIONS

Elderfield—"Heterocyclic Compounds"—vol. 5—Wiley & Sons, Inc.—(1957)—pp. 376–377.
Gompper et al.—Chem. Ber., 92, 1935 (1959).
Gompper—Chem. Ber. 89, 1748 (1956).

*Primary Examiner*—Anton H. Sutto
*Attorney, Agent, or Firm*—Connolly & Hutz

[57] ABSTRACT

The condensation of an α-halogen carbonyl compound with carbamic acid esters in the presence of a basic condensing agent and an aprotic solvent enables the production of oxazolinone-2-compounds in a high degree of purity, and in high yields in one step by using simple and readily available starting compounds.

11 Claims, No Drawings

PROCESS FOR THE PRODUCTION OF OXAZOLINONE-2-COMPOUNDS

This application is a continuation of U.S. application Ser. No. 725,323 filed Sept. 22, 1976 by Fritz Benker et al for "Process For The Production Of Oxazolinone-2-Compounds", now abandoned.

This invention relates to a process for the preparation of an oxazolinone-2 compound by the condensation of an α-halogencarbonyl compound with a carbamic acid ester.

In particular, the process according to the invention provides oxazolinone-2 compounds which are substituted in the 4- and/or 5-position by any organic radicals attached to the 4- or 5-position by a carbon atom. These substituents may be for example alkyl, aryl or heterocyclic radicals. They (the alkyl, aryl, or heterocyclic radicals) are linked to the 4- or 5-position either directly by a carbon atom (of the alkyl, aryl or heterocyclic radicals) that does not form non-aromatic double bond or indirectly by a carbonyl group.

It is known to prepare oxazolinone-2 compounds which are disubstituted in the 4- and 5-position by reacting α-hydroxyketones with carbamic acid esters or carbamic acid chlorides. One method has been described in B. 89, 1748 (1956). Oxazolinone-2 compounds disubstituted in the 4- and 5-position are also obtainable by a dipolar cyclo addition of alkenes with ethoxycarbonylazene as described in B 98, 2985 (1965). The ethoxycarbonylazene required for this reaction is prepared from an α-aminoketone by conversion into the corresponding α-azidoketo compounds and liberation of nitrogen by heat. The reaction of α-aminoketones with phosgene by the method described in J. org. chem. 23, 1572 leads to only moderate yields of oxazolinone-2 compounds substituted in the 4- and 5-position.

One disadvantage of the methods mentioned above is that the starting compounds required for the reactions, such as α-hydroxyketones and, to an even greater extent, aminoketones are difficult to obtain in a sufficiently pure state and in high yields.

It is therefore in practice necessary to find a new process by which oxazolinone-2-compounds substituted in the 4- and/or 5-position can be obtained in a high degree of purity and in high yields from simple and readily available starting compounds by a simple procedure.

It has been found that this problem can be reduced or substantially obviated by using α-halogen-carbonyl compounds and carbamic acid esters.

It is therefore among the objects of the present invention to provide a process for the preparation of an oxazolinone-2-compound by condensation of an α-halogen-carbonyl compound with a carbamic acid ester in the presence of an aprotic solvent and a basic condensing agent. Tertiary butylates of alkali metals being particularly suitable basic condensing agents for this purpose.

Other conventional basic condensing agents may also be used for the reaction according to the invention, provided that they are substantially anhydrous and free from protic solvents. The presence of small quantities of water or traces of other protic solvents is generally a disadvantage in the reaction according to the invention. It results in reduced yields or an increase in the number and percentage proportion of unwanted by-products, depending on the starting materials used. The last mentioned effect can be explained on the basis that the α-halogen ketone starting materials possibly more or less eliminates halogen and presumably may undergo further side reactions whereby this alteration of the starting material results in the formation of unwanted by-products.

The basic condensing agents used may also be alkali metals such as sodium or potassium, alkali metal hydrides or alkali metal alcoholates, provided that care is taken to ensure that they are used in an anhydrous state and substantially free from protic solvents. The preferred basic condensing agents used for the reaction according to the invention are alkali metal t-butylates, because of their ready availability and ease of handling since the commercial products are already substantially free from water and protic solvents. Among the above mentioned alkali metal hydrides and alkali metal alcoholates such as methylates, ethylates, isopropylates and t-butylates, the potassium compounds are preferred. In the reaction according to the invention, it is surprisingly found that in contrast to the reactions described in B 89, 1748 (1956), the halogen in the α-halogen-carbonyl compound is replaced by the nitrogen atom of the carbamic acid ester by nucleophilic attack and the ring closure reaction to form the oxazolinone-2 ring follows immediately.

The reaction according to the invention invariably gives rise to stereospecifically uniform oxazolinone-2 compounds which are isomers of the compounds obtained from the reaction of α-hydroxyketones with urethanes or isocyanates by the methods mentioned above using known starting compounds, wherein the position of the carbonyl group and of the α-hydroxyl group can be clearly identified. In the oxazolinone-2 compounds which are obtainable by the processes described in Ber. 89, 1748 (1956), the nitrogen atom of the oxazolinone-2 ring is directly attached to the carbon atom which was the carbon atom of the carbonyl group in the original starting material.

Oxazolinone-2 compounds can thus be prepared in a highly pure state and with excellent yields from simple and inexpensive starting materials by a single reaction step.

Suitable aprotic solvents include ethers, sulfoxides such as dimethylsulfoxide, nitriles such as acetonitrile, carboxylic or phosphoric acid amides, such as dimethyl formamide and hexamethylphosphoric acid triamide.

The reaction is preferably carried out at temperatures of from 20° to 200° C., more preferably 50° to 150° C.

Particularly suitable α-halogen ketone compounds for the reaction according to the invention are α-bromo- and α-chloroketone compounds.

Suitable carbamic acid esters for the reaction according to the invention are in particular carbamic acid alkyl, phenyl or benzyl esters, the alkyl group preferably having up to 4 carbon atoms. Carbamic acid ethyl ester is preferably used. According to the invention, the carbamic acid esters are preferably unsubstituted on the nitrogen atom. A corresponding ring closure reaction with formatiion of N-substituted oxazolinones takes place when the carbamic acid ester is singly substituted on the nitrogen atom. However, these N-substituted oxazolinones do not have the desired properties of yellow couplers.

The process is preferably carried out as follows: 1 to 3 Mol, preferably 1.5 to 2 mol of carbamic acid ester are dissolved in 6 to 15 times their volume quantity of an anhydrous aprotic solvent, preferably hexamethylphosphoric acid triamide, and heated on an oil bath to 50° to 150° C. together with 1 to 1.5 mol of an alkali metal t-butylate, preferably potassium t-butylate, with stirring. When the components have been homogeneously distributed, 1 mol of an α-halogen-carbonyl compound is introduced into the reaction mixture over a period of from 1 to 30 minutes and stirring is continued for 30 minutes to 3 hours at a reaction temperature of 50° to 150° C. The reaction mixture is processed by known methods, for example as follows:

The reaction mixture is poured out on 10 times its quantity of water to which 2 to 3 mol of acid, preferably glacial acetic acid, have been added. The solid precipitate which is in most cases formed can be suction filtered and purified by recrystallisation from organic solvents. If the required oxazolinone-2 compound precipitates as an oil, it is taken up in a solvent which is immiscible with water, such as ethyl acetate or benzene, and the solution is shaken several times with water. The oxazolinone-2 compound present in the residue left after evaporation of the solvent can be isolated in the pure form by known methods such as recrystallisation, chromatography or distillation. The yields obtained are between 40 and 90% of the theory, depending on the starting compound used.

At the given ratio of 1 to 3 mol of carbamic acid ester per mol of α-halogencarbonyl compound, the carbamic acid ester has little influence on the yield of oxazolinone-2 compound.

It is particularly advantageous to use a ratio of alkali metal t-butylate to α-halogencarbonyl compound of from 1:1 to 1.2:1.

Higher yields can generally be obtained by using potassium t-butylate than by using sodium t-butylate.

The α-halogencarbonyl compound should be added as rapidly as possible and, as far as possible, undiluted.

Suitable α-halogencarbonyl compounds for the reactions according to the invention are in particular compounds of the following formulae (I)

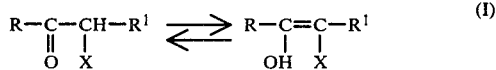
(I)

in which

X represents halogen such as chlorine or bromine;

R or R¹ represents hydrogen or

R and/or R¹, which may be the same or different, represent alkyl, aryl or heterocyclic groups which may carry any substituents and are attached to the carbon atoms of formula (I) through a carbon atom of the aforesaid groups or through a carbonyl group.

In particular, R and/or R¹ may represent the following groups: Aliphatic or aromatic hydrocarbon groups, a heterocyclic group or the group COR² in which R² represents hydroxyl, alkoxy, aroxy, alkyl, aryl, a heterocyclic group or an amino group which may be monosubstituted or disubstituted by alkyl, aryl or heterocyclic groups, and in the case of a disubstituted amino group the substituents may represent the atoms required for closing a 5- or 6-membered heterocyclic ring.

If in the above formula I the groups R, R¹ or R² represent or contain alkyl, they are straight or branched chain alkyl groups having from 1 to 20 carbon atoms, such as methyl, isopropyl, butyl, t-butyl, octyl, dodecyl, hexadecyl groups or substituted alkyl groups such as benzyl or phenethyl.

In cases where R and/or R¹ represent cycloalkyl groups, they are 5- or 6-membered hydrocarbon groups which may in turn be substituted by alkyl groups and may have, in particular from 5 to 20 carbon atoms, e.g. cyclohexyl, cyclopentyl or 7,7-dimethylnorbornyl.

In cases where R, R¹ or R² represent or contain aryl groups they are aryl groups such as naphthyl or phenyl groups, in particular phenyl groups, which may be substituted by one or more substituents, for example by alkyl, alkoxy, alkylamino or alkylthio, in any of which the said alkyl groups may contain from 1 to 20 carbon atoms, nitro, halogen such as fluorine, chlorine or bromine, carboxyl, sulfo, acyl or acylamino in which the acyl groups may be derived from aliphatic or aromatic carboxylic or sulphonic acids or carbonic acid monoesters or carbamic acid, such as heptadecylcarbonamido, dimethylaminosulfonyl, phenyloctadecylaminosulfonyl, methyloctadecylaminocarbonyl, phenylaminocarbonyl, benzoylamino, phenoxycarbonyl or alkoxycarbonyl.

Where the groups R, R¹ or R² represent or contain heterocyclic groups, they are preferably 5- or 6-membered heterocyclic groups, in particular those having at least one nitrogen atom, e.g.: pyridyl, thiazolyl, morpholine, furanyl or indole groups.

The following are mentioned as examples of α-halogen carbonyl compounds which may be reacted according to the invention to form oxazolinone-2 compounds:

Chloracetone;
2-chlorobutanone-(3);
chloromethyl-isopropylketone;
4-chloro-octanone-(5);
α-chloro-acetophenone;
α-chloro-propiophenone;
α-chloro-butyrophenone;
α-chlorophenylacetaldehyde;
desyl chloride;
1-chloro-2-oxo-1,2-dicyclohexyl-ethane;
α-chloro-benzyl-(4-fluorophenyl)-ketone;
(α-chloro-4-methoxybenzyl)-(4-methoxyphenyl)-ketone;
(α-chloro-4-nitrobenzyl)-(4-methoxyphenyl)-ketone;
α-chloro-benzyl-(4-N,N-dimethylaminophenyl)-ketone;
1-chloro-2-oxo-1,2-di-α-pyridyl-ethane;
1-chloro-2-oxo-1-quinazolinonyl-(2)-2-p-tolyl-ethane;
(α-chloro-4-acetaminobenzyl)-(2,4-dimethoxyphenyl)-ketone;
α-chloro-benzyl-(4-tetradecyloxyphenyl)-ketone;
(α-chloro-4-cetyloxycarbamidobenzyl)-(4-methoxyphenyl)-ketone;
chloromethyl-(3-stearoylaminophenyl)-ketone;
(α-chloro-4-N-methyl-N-octadecylaminobenzyl)-(2,4-dimethoxyphenyl)-ketone;
α-bromo-4-cetyloxy-acetophenone;
2-chloro-1,3-dioxo-1-phenyl-butane;
3-bromo-1,2-dioxo-1-phenyl-propane;
3-bromo-1,2-dioxo-1-phenyl-butane;
1-chloro-2,3-dioxo-butane;
3-chloro-1,2-dioxo-1-p-tetradecyloxyphenyl-butane;
2-chloro-1,3-dioxo-1,3-di-(o-decyloxyphenyl)-propane;
2-chloro-1,3-dioxo-1-(o-tetradecyloxyphenyl)-butane;
α-chloro-acetic acid ethyl ester;
α-chloro-pivaloylacetic acid ethyl ester;
α-chloro-myristoylacetic acid ethyl ester;
α-chloro-benzoylacetic acid ethyl ester;
α-chloro-o-chlorobenzoylacetic acid ethyl ester;
α-chloro-p-chlorobenzoylacetic acid ethyl ester;
α-chloro-o-fluorobenzoylacetic acid ethyl ester;

α-chloro-benzoylacetic acid phenyl ester;
α-chloro-m-nitrobenzoylacetic acid ethyl ester;
α-chloro-p-nitrobenzoylacetic acid ethyl ester;
α-chloro-o-methoxybenzoylacetic acid ethyl ester;
α-chloro-m-methoxybenzoylacetic acid ethyl ester;
α-chloro-p-methoxybenzoylacetic acid ethyl ester;
α-chloro-2,5-dimethoxybenzoyl acetic acid ethyl ester;
α-chloro-2-phenoxy-propionyl-(2)-acetic acid ethyl ester; α-chloro-thienyl-2-oyl-acetic acid ethyl ester;
α-chloro-furyl-2-oyl-acetic acid ethyl ester;
α-chloro-naphthyl-2-oyl-acetic acid ethyl ester;
α-chloro-bornyl-2-oyl-acetic acid ethyl ester;
α-chloro-o-tetradecyloxy-benzoylacetic acid methyl ester;
α-chloro-o-tetradecyloxy-benzoylacetic acid phenyl ester;
α-chloro-p-tetradecyloxy-benzoylacetic acid ethyl ester;
α-chloro-p-cetyloxybenzoyl-acetic acid phenyl ester;
phenylene-1,4-bis-(α-chloro-β-oxo-propionic acid ethyl ester);
bromopyruvic acid ethyl ester;
3-chloro-2-oxo-butyric acid methyl ester;
3-chloro-2-oxo-4-methyl-pentanoic acid ethyl ester;
3-chloro-2-oxo-4,4-dimethyl-pentanoic acid methyl ester;
3-chloro-2-oxo-4,4-dimethyl-pentanoic acid-t-butyl ester;
3-chloro-2-oxo-nonanoic acid methyl ester;
3-chloro-2-oxo-arachidic acid methyl ester;
3-chloro-2-oxo-3-phenyl-propionic acid methyl ester;
3-chloro-2-oxo-3-phenyl-propionic acid t-butyl ester;
3-chloro-2-oxo-3-o-chlorophenyl-propionic acid methyl ester;
3-chloro-2-oxo-3-m-chlorophenyl-propionic acid methyl ester;
3-chloro-2-oxo-3-o-fluorophenyl-propionic acid methyl ester;
3-chloro-2-oxo-3-m-nitrophenyl-propionic acid methyl ester;
3-chloro-2-oxo-3-m-tolyl-propionic acid methyl ester;
3-chloro-2-oxo-3-o-methoxyphenyl-propionic acid methyl ester;
3-chloro-2-oxo-3-o-methoxyphenyl-propionic acid t-butyl ester;
3-chloro-2-oxo-4-p-tolyl-butyric acid methyl ester;
3-chloro-2-oxo-3-(3,5-dichloro-2-methoxyphenyl)-propionic acid methyl ester;
3-chloro-2-oxo-3-(3,5-dichloro-2-tetradecyloxyphenyl)-propionic acid methyl ester;
3-chloro-2-oxo-3-(3,4-methylenedioxyphenyl)-propionic acid methyl ester;
3-chloro-2-oxo-3-o-tetradecyloxyphenyl-propionic acid methyl ester;
3-chloro-2-oxo-3-o-tetradecyloxyphenyl-propionic acid t-butyl ester;
3-chloro-2-oxo-3-p-cetyloxyphenyl-propionic acid methyl ester;
3-chloro-2-oxo-3-m-palmitoylamidophenyl-propionic acid methyl ester;
3-chloro-2-oxo-3-p-carbethoxyphenyl-propionic acid methyl ester;
3-chloro-2-oxo-3-pyridyl-(2)-propionic acid methyl ester;
phenylene-1,3-bis-(β-chloro-α-oxo-propionic acid methyl ester);
α-chloro-acetyl-acetanilide,
α-chloro-pivaloyl-aceto-N-methylanilide,
α-chloro-myristoyl-aceto-(2-chloro-5-nitroanilide);
α-chloro-benzoyl-acetomorpholide,
α-chloro-benzoyl-aceto-N-methyl-p-toluidide;
α-chloro-benzoyl-aceto-N,N-dibutylamide;
α-chloro-o-methoxybenzoyl-acetanilide;
α-chloro-o-chlorobenzoyl-aceto-o-tetradecyloxyanilide;
α-chloro-o-methoxybenzoyl-aceto-N-methyl-o-tetradecyloxyanilide;
α-chloro-benzoyl-aceto-N-methyl-N-octadecylanilide,
α-chloro-o-fluorobenzoyl-acetanilide;
α-chloro-o-tetradecyloxybenzoyl-acetomorpholide;
α-chloro-o-tetradecyloxybenzoyl-aceto-N-methylanilide;
α-chloro-o-tetradecyloxybenzoyl-aceto-o-methoxyanilide;
α-chloro-o-tetradecyloxybenzoyl-aceto-N,N-dibutylamide;
α-chloro-benzoyl-aceto-(4-N-phenyl-N-octadecylsulfamyl anilide);
α-chloro-benzoyl-aceto-(2-cetyloxy-5-N,N-dimethylsulfamyl anilide);
bis-(α-chloro-o-tetradecyloxybenzoyl-aceto)-1,4-phenylene diamide;
α-chloro-benzoyl-aceto-o-tetradecyloxyanilide.

Other commonly known α-halogen-β-ketomethylene yellow coupler compounds may, of course, also be reacted to form the couplers according to the invention. Examples of suitable α-halogen-β-ketomethylene yellow coupler compounds have been described in U.S. Pat. Nos. 2,728,658; 3,265,508; 3,664,841; 3,615,606 and 3,849,140 and 3,770,446.

α-Halogencarbonyl compounds of the general formula I are known per se and where they are not commercially obtainable they can be prepared by the following general methods:

(A) Chlorination of α-hydroxyketones with thionyl chloride;

(B) Halogenation of keto compounds with the following halogenating agents:
(a) sulfuryl chloride,
(b) halosuccinimide such as chlorosuccinimide or bromosuccinimide or
(c) halogens such as chlorine or bromine;

(C) Ester condensation, for example α-chloro-β-ketosuccinic acid ethyl ester can be obtained by the reaction of oxalic acid diethylester with ethyl chloroacetate in the presence of sodium ethylate in accordance with the following reaction scheme:

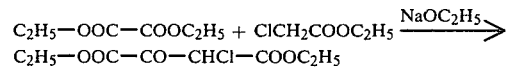

(D) Darzens condensation described by MacDonald and Schwab in Org. Chem. 29, 2459 (1964), in which aldehydes react with dichloroacetic acid esters in the presence of sodium methylate via the state of the α-chloropoxide and rearrangement into the β-chloro-α-carbonylcarboxylic acid ester in accordance with the following reaction scheme:

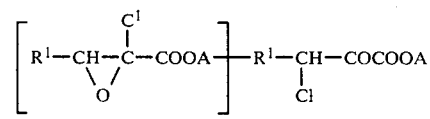

in which

A represents alkyl or aryl and

R¹ has the meaning as defined above for the general formula I.

Compounds with the oxazolinone-2 structure which can be prepared according to the invention constitute a group of particularly active coupler compounds for photographic purposes.

Introduction of the cyanate group (N—C—O) with formation of the oxazolinone-2 structure makes it possible for the carbon atom of the originally present carbonyl group to undergo a coupling reaction with oxidized color developer substance. The advantage of introducing the cyanate group into α-halogen carbonyl compounds to form oxazolinone-2 compounds which are capable of coupling reactions is illustrated below with the aid of a simple example. Compounds of the structure

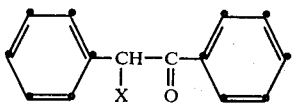

in which X represents hydrogen, halogen or hydroxyl, do not couple with oxidized color developer substances of the p-phenylenediamine structure to produce azo methine dyes because the phenyl group adjacent to the substituted methylene group does not sufficiently activate the coupling reaction. Reaction of the compound of the above structure with carbamic acid ester results in a 4,5-diphenyloxazolinone-2 which couples readily and easily to form a brilliant yellow dye.

Oxazolinone-2 prepared according to the invention and its derivatives substituted in the 4- and/or 5-position as defined above are therefore suitable for use as color couplers for photographic silver halide materials.

The following are given as examples of oxazolinone-2 compounds which are obtainable according to the invention:

(1) 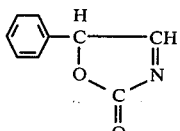

(2) 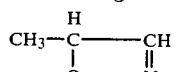

(3) 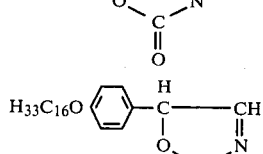

(4) 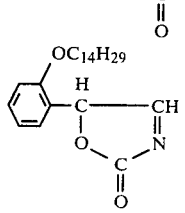

-continued (5) 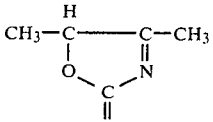

(6) 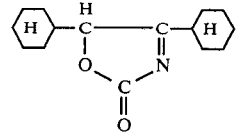

(7) 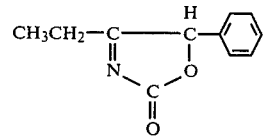

(8) 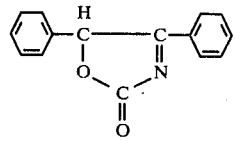

(9) 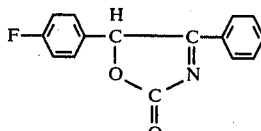

(10) 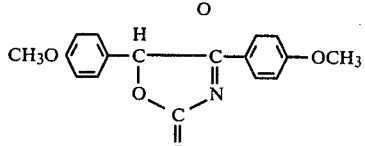

(11) 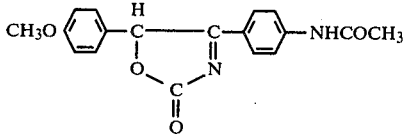

(12) 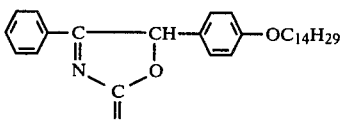

(13) 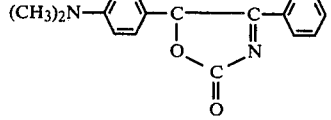

(14) 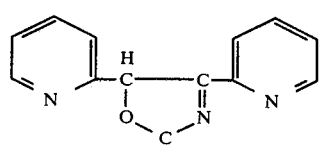

(15) 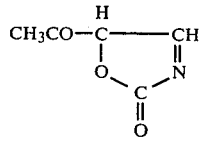

(16) 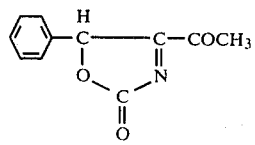

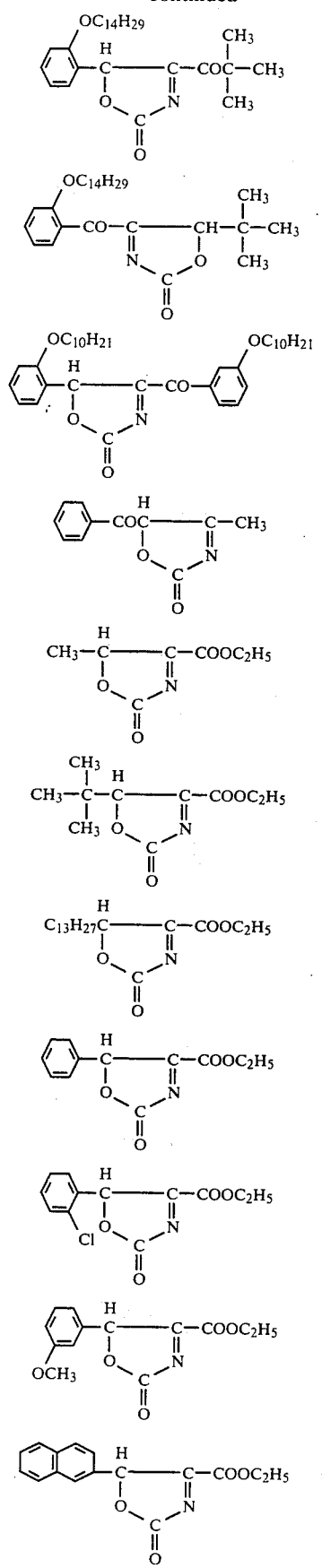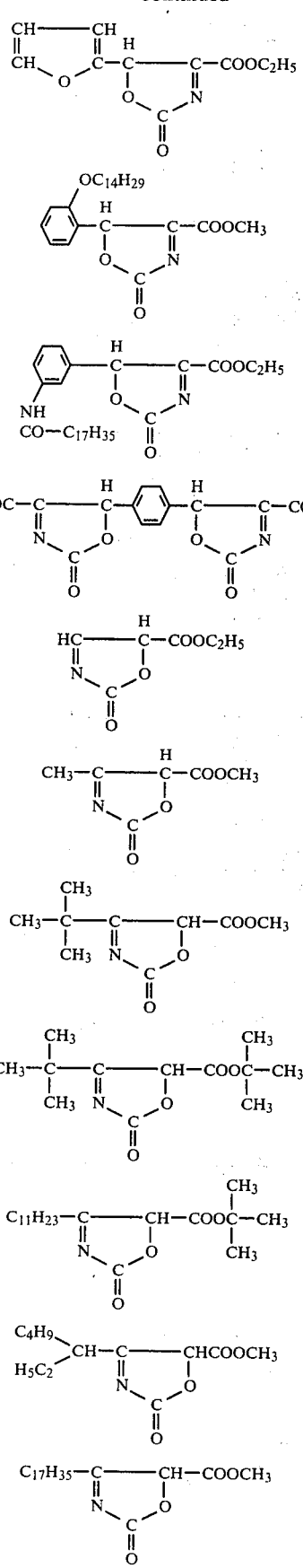

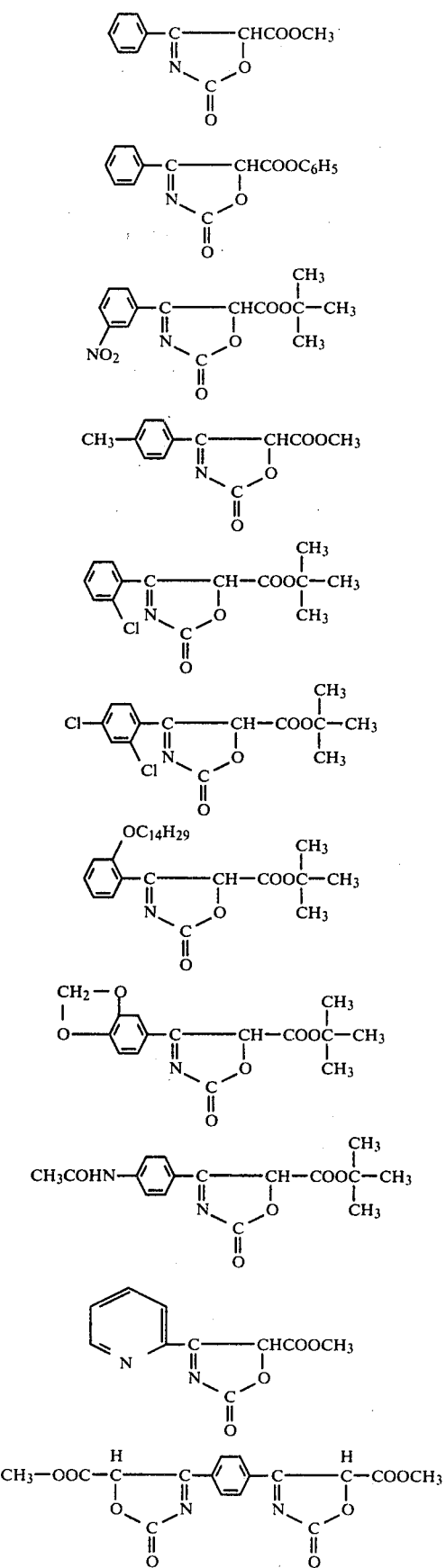

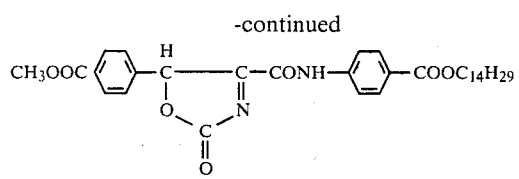

(60)

The method of preparation according to the invention will now be described in detail with reference to specific coupler compounds:

Preparation 1 (Compound 3)

5-(4-Cetyloxyphenyl)-oxazolinone-2

Stage 1

23 g of 4-acetyloxybenzoylacetic acid ethyl ester were boiled under reflux for 5 hours in 70 ml of alcohol in the presence of 3.3 g of sodium hydroxide. After cooling of the reaction mixture, the resulting precipitate was suction filtered and recrystallized from methanol.

The yield was 12 g of cetyloxyacetophenone with an m.p. of 62° to 64° C.

Stage 2

7.2 g of the compound prepared in Stage 1 were dissolved in 75 ml of benzene. 3.2 g of bromine in 5 ml of benzene were added dropwise with stirring at 25° C. After decolorization, the reaction phase was free from the resulting acid by the addition of water. The benzene phase was then separated and benzene distilled off. The residue was recrystallized from glacial acetic acid.

The yield was 6.7 g of α-bromo-cetyloxy-acetophenone with an m.p. of 66° to 68° C.

Stage 3

A mixture of 1.8 g of urethane, 20 ml of hexamethyl phosphoric acid triamide and 1.12 g of potassium t-butylate was stirred on a heating bath which was at a temperature of 90° C. until a pale brown suspension was formed. 4.39 g of the compound obtained in Stage 2 were then added and the mixture stirred for a further 3 hours at 90° C. The reaction mixture was then poured into water and acidified with glacial acetic acid. The resulting precipitate was suction filtered. The crude product was purified by recrystallization from ethyl acetate.

The yield was 2 g of compound No. 3 (50% of theory) with an m.p. of 174° to 176° C.

Preparation 2 (Compound No. 22)

4-Carbethoxy-5-t-butyl-oxazolinone-2

Stage 1

A mixture of 13.5 g of sulfuryl chloride and 10 ml of glacial acetic acid was added over a period of 30 minutes to a solution of 17.2 g of pivaloyl acetic acid ethyl ester and 8.5 g of sodium acetate sicc. in 160 ml of glacial acetic acid at 35° C. The reaction solution was poured into water after a further 70 minutes and the oily layer was taken up with ethyl acetate. After repeated washing of the solvent layer, the ethyl acetate layer was separated and concentrated by evaporation under vacuum. The oily residue containing α-chloro-pivaloylacetic acid ethyl ester was used without further purification.

Stage 2

A mixture of 13.5 g of urethane, 150 ml of hexamethyl phosphoric acid triamide and 11.2 g of potassium p-butylate was stirred at 120° C. until a pale brown suspension had formed. The oily residue obtained in Stage 1 was then added and the mixture stirred for a further hour at 120° C. The reaction mixture was then poured out on water and the precipitated oil was taken up with ethyl acetate after acidification with glacial acetic acid. The product was processed as described for Stage 1. Evaporation of the solvent left an oily residue which crystallized when left to stand for some time.

The yield was 14 g of compound No. 22 with an m.p. of 77° to 78° C.

Preparation 3 (Compound No. 35)

4-t-Butyl-5-t-butyloxy-carbonyl-oxazolinone-2

Stage 1

74 g of t-butanol, 79 g of pyridine and 250 ml of anhydrous ether were heated to boiling and 146 g of dichloroacetyl chloride were added dropwise to the reaction mixture at such a rate that the reaction mixture continued to boil without further application of heat. When all the dichloroacetyl chloride had been added, boiling was continued for 3 hours and water was then added to the reaction mixture and the ethereal phase separated off. The reaction solution obtained in this way was processed in the usual manner, for example as described for preparation 1 or 2.

The yield was 140 g of α,α-dichloroacetic acid t-butyl ester.

Stage 2

86 g of pivalaldehyde were added slowly at −25° C. to a suspension of 112 g of potassium t-butylate in 600 ml of butyl chloride. A mixture of 185 g of dichloroacetic acid t-butyl ester obtained in stage 1 and 200 ml of butyl chloride was added slowly so that the temperature did not rise above −15° C. After continued stirring for a further 3 hours, the reaction mixture was poured on water and acidified with glacial acetic acid. The butyl chloride layer was washed several times with water, dried and freed from solvent. The residue was fractionated over a fractionating column at 0.1 Torr.

The yield was 150 g of 3-chloro-2-oxo-4,4-dimethyl-pentanoic acid-t-butyl ester with a b.p.$_{0.1\ mm}$ of 60° C.

Stage 3

A mixture of 18 g of urethane, 150 ml of hexamethyl phosphoric acid triamide and 11.2 g of potassium t-butylate, was reacted with 23.4 g of the compound from stage 2 at a bath temperature of 150° C. The product was processed as described for preparation 1, stage 3, except that the crystalline precipitate was treated only with petroleum hydrocarbons.

The yield was 12 g of compound No. 35 (50% of the theory) with an m.p. of 208° C. Stage 3 was repeated using other basic condensing agents instead of potassium t-butylate. The following were used in place of 11.2 g of potassium t-butylate:

|  | Yield of compound 35 |
| --- | --- |
| (a) 2.3 g of sodium | 6 g |
| (b) 3.9 g of potassium | 11.5 g |
| (c) 2.4 g of sodium hydride | 4 g |
| (d) 2.3 g of sodium dissolved in CH$_3$OH and the solution evaporated to dryness | 4 g |
| (e) 4 g of solid sodium hydroxide | 2.5 g |

Preparation 4 (Compound No. 41)

4-(3-nitrophenyl)-5-t-butyloxycarbonyl-oxazolinone-2

Stage 1

15.1 g of m-nitrobenzaldehyde were dissolved in 200 ml of ether. 13.5 g of potassium t-butylate were slowly introduced at −25° C. with stirring. 18.5 g of α,α-dichloroacetic acid t-butyl ester prepared according to preparation 3, stage 1 were added dropwise to the resulting suspension over a period of 20 minutes. After a further reaction time of 2 hours at −25° C., the reaction mixture was neutralized with glacial acetic acid. Water was then added. The ethereal layer was then processed in the usual manner. The residue was recrystallized from butyl chloride/petroleum hydrocarbons.

The yield was 18 g of 3-chloro-2-oxo-3-m-nitrophenyl-propionic acid-t-butyl ester with an m.p. of 76° to 78° C.

Stage 2

A mixture of 18 g of urethane, 150 ml of hexamethyl phosphoric acid triamide and 11.2 g of potassium t-butylate was reacted at a bath temperature of 80° C. with 30.0 g of the compound prepared in stage 1. After a reaction time of 1.5 hours, the reaction mixture was poured on water and the precipitated oil was processed using ethyl acetate as described for preparation 2. Compound 41 was isolated from the residue by crystallization from butyl chloride.

The yield was 9 g of compound 41 (30% of the theory) with an m.p. of 147° to 149° C.

Preparation 5 (Compound No. 45)

4-(2-Tetradecyloxyphenyl)-5-tert.butyloxy-carbonyl-oxazolinone-2

Stage 1

122 g of salicylic aldehyde and 287 g of n-tetradecyl bromide were added to a solution of 40 g of sodium hydroxide in 600 ml of methyl glycol and the reaction mixture was boiled with stirring for 6 hours. It was then poured out on water and the resulting oily layer was separated and taken up with methylene chloride. The methylene chloride phase was then washed and processed in the usual manner. The residue was crystallized from methanol to which a small quantity of isopropanol had been added.

The yield was 300 g of 2-tetradecyloxy-benzaldehyde with an m.p. of 41° C.

Stage 2

The preparation of 3-chloro-2-oxo-3-(o-tetradecyloxyphenyl)-propionic acid-t-butyl ester was carried out as described in preparation 4, stage 1, except that instead of 15.1 g of m-nitrobenzaldehyde, 31.8 g of 2-tetradecyloxybenzaldehyde were used. The residue was used without further purification.

Stage 3

A mixture of 18 g of urethane, 150 ml of hexamethyl phosphoric acid triamide and 11.2 g of potassium t-butylate were reacted at 150° C. with the residue obtained in Stage 2. After the product had been processed in the usual manner as described in preparations 1 to 5, 42 g of a slowly solidifying residue were obtained. This residue was purified by column chromatography.

The yield was 37 g of compound No. 45 (80% of the theory) with an m.p. of 60° to 61° C.

Preparation 6 (Compound No. 53)

4-Phenyl-5-(2-tetradecyloxianilido)-oxazolinone-2

Stage 1

α-Chloro-benzoylaceto-o-tetradecyloxianilide was prepared by a similar method to that described in example of preparation 2, stage 1. The compound had a melting point of 71° to 72° C.

Stage 2

A mixture of 18 g (0.2 mol) of urethane, 150 ml of hexamethylphosphoric acid triamide and 0.1 mol of potassium t-butylate was reacted with 0.1 mol of the compound obtained in Stage 1 at a bath temperature of 80° C. The reaction time and method of processing the reaction product were the same as described for the preparation of Stage 3. Recrystallization from ethyl acetate.

The yield was 43.5 g of compound No. 53 (88% of the theory) with an m.p. of 132° C.

Some of the compounds prepared by the process according to the invention, in particular those which carry a carboxyl or alkoxycarbonyl group in the 4- and/or 5-position, are suitable for the preparation of other oxazolinone yellow couplers. The usual known methods are employed for this purpose and it is not necessary to refer to them in detail. Examples have been fully described in U.S. Pat. No. 4,059,447.

The process of preparation according to the invention can therefore be used in particular for the preparation of compounds of the following general formula (II) or their tautomeric compounds:

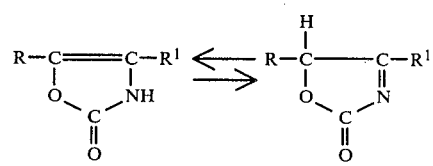

in which R and R$^1$ have the meanings specified above.

As already indicated, the compounds prepared according to the invention are suitable for photographic purposes. When used in color photographic materials containing at least one silver halide emulsion layer, the compounds prepared according to the invention are capable of entering into a coupling reaction with aromatic developer substances containing primary amino groups. Compounds having the oxazolinone-2 structure are surprisingly found to constitute a group of exceptionally active coupler compounds. Those compounds of the above formula (I) in which R and R$^1$ are different from each other are preferred for photographic purposes.

Those coupler compounds prepared according to the invention which do not carry a longer chain substituent are preferably used in developer solutions as couplers which are not resistant to diffusion. Examples of such couplers are, among others, compounds 16, 20, 25 and 26.

Examples of couplers which are resistant to diffusion when incorporated in photographic material contain at least one group which confers diffusion resistance.

Groups are regarded as conferring diffusion resistance if they make it possible for the compounds according to the invention to be incorporated without risk of diffusion in the hydrophilic colloids conventionally used in photographic materials. Among these groups are included preferably organic groups which are generally straight or branched chain aliphatic groups and which may also contain isocyclic or heterocyclic aromatic groups. The aliphatic part of these groups generally contains from 8 to 20 carbon atoms. These groups are attached to the remaining part of the molecule either directly or indirectly, for example by way of one of the following groups: CONH, SO$_2$NH, CO, SO$_2$, O, S or NR', where R' represents hydrogen or alkyl.

In addition, the group which confers diffusion resistance may also contain groups which confer solubility in water, e.g. sulfo groups or carboxyl groups, and these may also be present in an anionic form. Since the diffusion properties depend on the molecular size of the total compound, it is sufficient in certain cases, for example if the molecule as a whole is sufficiently large, to use shorter chain groups for conferring diffusion resistance, e.g. one or more t-butyl, cycloalkyl or isoamyl groups.

Examples of couplers which can be incorporated in a diffusion fast form in the hydrophilic colloid layer of a light-sensitive photographic material include among others compounds 17 to 19, 30, 55 to 58 and 60.

The use of oxazolinone-2 compounds obtainable by the process according to the invention in photographic materials has been described in some detail in U.S. Pat. No. 4,059,447 and the suitability of these compounds as color couplers and in particular as yellow couplers has been fully explained.

Compared with the process described in U.S. Pat. No. 4,059,447 the process according to the invention is distinguished by the advantageous increase in yield. The yield of compound 41, for example, can be increased by about 20% by the process according to the invention while the yields of compounds 3 and 22 can be increased by as much as about 30%.

When preparing the light-sensitive color photographic material, the diffusion resistant couplers according to the above general formula prepared according to the invention can be added to the casting solutions for the silver halide emulsion layers or other colloid layers. For example, water-soluble color couplers, i.e. those containing one or more water-solubilizing groups such as sulfo or carboxyl groups (in the acid or salt form) may be added as aqueous solutions while the color couplers which are insoluble in water or not sufficiently soluble in water may be added in the form of a solution in suitable water-miscible or water immiscible high boiling or low boiling organic solvents or mixtures thereof. The resulting solution is then dispersed in known manner in an aqueous colloid solution, e.g. a gelatine solution, in the presence of a wetting or dispersing agent. The aqueous hydrophilic colloid solution may, of course, also contain other additives. Water insoluble color couplers containing fluorosulfonyl groups or carboxylic acid ester groups such as ethoxycarbonyl groups may also be converted into the corresponding sulfonic acids or carboxylic acids by alkaline hydrolysis and then used as aqueous solution, e.g. in the form of their alkali metal salts.

The solution of color coupler need not be directly dispersed or dissolved in the casting solution of the silver halide emulsion layer or of another water permeable layer but may advantageously first be dispersed or dissolved in an aqueous solution of a hydrophilic colloid which is not sensitive to light, whereupon the resulting mixture may be carefully mixed with the casting solution of the light-sensitive silver halide emulsion layer or of some other water-permeable layer before it is applied, if necessary after removal of the organic solvent used. Further information, particularly concerning suitable techniques for incorporating color couplers in hydrophilic colloid layers of a photographic material, may be found in the published Dutch Patent Applications No. 6,516,423; No. 6,516,424; No. 6,600,098; No. 6,600,099 and No. 6,600,628; Belgian Patent Specification No. 750,889; U.S. Pat. No. 2,304,940 and British Patent Specification No. 791,219.

Those among the color couplers prepared according to the invention which are not resistant to diffusion can easily be added as aqueous solutions or with the aid of small quantities of aliphatic alcohols to the usual color developer solutions used for the so-called method of development of incorporation.

To produce photographic color images, an exposed silver halide emulsion layer is developed with an aromatic primary amino developer substance in the presence of one of the color couplers prepared according to the invention. Any color developer substances capable of yielding azomethine dyes may be used as developer substances. Suitable developer substances include aromatic compounds such as p-phenylene diamine and its derivatives, for example N,N-dialkyl-p-phenylenediamine such as N,N-diethyl-p-phenylenediamine, N,N-dialkyl-N'-sulphomethyl-p-phenylene diamines and N,N-dialkyl-N'-carboxymethyl-p-phenylenediamines.

Suitable for use as light-sensitive emulsions are emulsions of silver halides such as silver chloride, silver bromide or mixtures thereof, which may have a small silver iodide content of up to 10 mol %, in one of the usual hydrophilic binders. The binder used for photographic layers is preferably gelatine although this may be partly or completely replaced by other natural or synthetic binders. Suitable natural binders include e.g. alginic acid and its derivatives such as salts, esters or amides; cellulose derivatives such as carboxymethylcellulose; alkyl celluloses such as hydroxyethylcellulose; starch and its derivative such as ethers or esters and carrageenates. Suitable synthetic binders include polyvinyl alcohol, partially saponified polyvinyl acetate and polyvinyl pyrrolidone.

The emulsions may also be chemically sensitized, for example by the addition of sulfur compounds such as allylisothiocyanate, allylthiourea and sodium thiosulfate at the chemical ripening stage. Reducing agents may also be used as chemical sensitizers, for example the tin compounds described in Belgian Patent Specifications No. 493,464 and No. 568,687 or polyamides such as diethylenetriamine or aminomethanesulfinic acid derivatives e.g. according to Belgian Patent Specification No. 547,323.

Noble metals such as gold, platinum, palladium iridium, ruthenium and rhodium and compounds of these metals are also suitable chemical sensitizers. This method of chemical sensitization has been described in the article by R. KOSLOWSKY, Z. wiss. Phot. 46, 65 to 72 (1951).

The emulsions may also be sensitized with polyalkylene oxide derivatives e.g. with a polyethylene oxide having a molecular weight of between 1,000 and 20,000 or with condensation products of alkylene oxides and aliphatic alcohols, glycols, cyclic dehydration products of hexitols, alkyl-substituted phenols, aliphatic carboxylic acids, aliphatic amines, aliphatic diamines and amides.

The condensation products have a molecular weight of at least 700, preferably more than 1,000. These sensitizers may, of course, be combined to produce special effects as described in Belgian Patent Specification No. 537,278 and British Patent Specification No. 727,982.

The compounds prepared according to the invention are preferably used in blue-sensitive emulsions. These emulsions must be sufficiently sensitive to the blue region of the spectrum. The emulsions used for this purpose have generally not been sensitized, their sensitivity being due to the intrinsic sensitivity of the silver halides in them, but the silver halide emulsions may also be sensitized to the blue spectral region if desired, for example using sensitizers of the kind described in German Offenlegungsschrift No. 1,808,041.

The emulsions may contain the usual stabilizers, e.g. homopolar compounds or salts of mercury having aromatic or heterocyclic rings, such as mercapto triazoles, simple mercury salts, sulfonium mercury double salts and other mercury compounds. Azaindenes are also suitable stabilizers particularly tetra- and penta-azaindenes and especially those which are substituted with hydroxyl or amino groups. Compounds of this kind have been described in the article by BIRR, Z. wiss. Phot. 47, 2 to 27 (1952). Other suitable stabilizers include heterocyclic mercapto compounds e.g. phenylmercaptotetrazole; quaternary benzothiazole derivatives and benzotriazole.

The emulsions may be hardened in the usual manner, for example with formaldehyde or halogen substituted aldehydes which contain a carboxyl group such as mucobromic acid; diketones; methanesulfonic acid esters and dialdehydes.

The photographic layers may also be hardened with epoxide hardeners, heterocyclic ethyleneimine or acryloyl hardeners. Examples of such hardeners have been described, for example, in German Offenlegungsschrift No. 2,263,602 and in British Patent Specification No. 1,266,655. The layers may also be hardened by the process according to German Offenlegungsschrift No. 2,218,009 for producing color photographic materials which are suitable for high temperature processing.

The photographic layers or color photographic multi-layered materials may also be hardened with hardeners based on diazine, triazine or 1,2-dihydroquinoline as described in British Patent Specification Nos. 1,193,290; 1,251,091; 1,306,544 and 1,266,655; French Patent Specification No. 7,102, 716 and Belgian Patent No. 816 410. Examples of such hardeners include diazine derivatives containing alkyl or arylsulfonyl groups; derivatives of hydrogenated diazines or triazines such as 1,3,5-hexahydrotriazine; fluorosubstituted diazine derivatives such as fluoropyrimidines and esters of 2-substituted 1,2-dihydroquinoline- or 1,2-dihydroisoquinoline-N-carboxylic acid. Vinyl sulphonic acid hardeners, carbodiimide hardeners and carbamoyl hardeners such as those described e.g. in German Offenlegungsschrift No. 2,263,602; French Patent Specification Nos. 2,185,807, 1,599,038 and 1,491,807; German Patent Specification No. 872,153 and DDR Patent Specification No. 7,218 are also useful. Other suitable hardeners have been described for example, in British Patent specification No. 1,268,550.

The oxazolinone-2 compounds may be used for the preparation of conventional positive, negative or reversal materials on the usual support layers such as foils of cellulose triacetate; cellulose acetate; cellulose nitrate; polystyrene; polyesters such as polyethylene terephthalate and polyolefines such as polyethylene or polypropylene, baryta paper substrates or polyolefine laminated paper substrates such as polyethylene laminated substrates as well as glass.

We claim:

1. The process of preparing a 3-oxazolinone-2-compound or its tautomeric form in which a α-halogen carbonyl compound of the formula

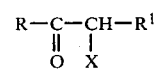

in which
X represents chlorine or bromine
R and $R^1$ are each selected from the group consisting of hydrogen, alkoxy carbonyl groups, N-arylcarbamoyl, N-alkyl-N-arylcarbamoyl, N,N-dialkylcarbamoyl, morpholinocarbonyl
straight or branched chain alkyl groups having from 1-20 carbon atoms, 5- or 6-membered cycloalkyl groups which may in turn be substituted by alkyl groups, the alkyl-cycloalkyl entity having from 5-20 carbon atoms,
naphthyl or phenyl groups and heterocyclic groups selected from the group consisting of pyridyl, thiazolyl, morpholine, furanyl and indole,
which alkyl, naphthyl, phenyl and heterocyclic groups are attached to the carbons of the above formula either directly through a carbon of said groups or indirectly through a carbonyl group,
but not more than one of R and $R^1$ may be hydrogen,
is condensed in a reaction mixture with a carbamic acid ester selected from the group consisting of alkyl, phenyl and benzyl esters of carbamic acid, in the presence of an aprotic solvent and a basic condensing agent selected from the group consisting of an alkali metal, an alkali metal hydride and an alkali metal alcoholate at a temperature of between 20° C. and 200° C.

2. Process according to claim 1, wherein the aprotic solvent used is a polar solvent.

3. Process according to claim 1, wherein the aprotic solvent used is an ether, sulfoxide, nitrile or acid amide or combination thereof.

4. Process according to claim 3, wherein the acid amide is selected from the group consisting of dimethyl foramide and hexamethyl phosphoric acid triamide.

5. Process according to claim 1, wherein the aprotic solvent used is hexamethylphosphoric acid triamide.

6. Process according to claim 1, wherein the basic condensing agent used is an alkali metal t-butylate.

7. Process according to claim 1, wherein the basic condensing agent used is potassium metal, potassium hydride or a potassium alcoholate.

8. Process according to claim 6, wherein 1 to 1.2 mol of alkali metal t-butylate is used per mol of α-halogen carbonyl compound.

9. Process according to claim 1, wherein 1 to 3 mol of carbamic acid ester is used per mol of α-halogen carbonyl compound.

10. Process according to claim 6, wherein the alkali metal t-butylate used is potassium t-butylate.

11. Process according to claim 7, wherein the α-halogen carbonyl compound is an α-halogen ketone.

* * * * *